(12) United States Patent
Reynoso et al.

(10) Patent No.: US 11,338,053 B2
(45) Date of Patent: May 24, 2022

(54) ANTIMICROBIAL SYSTEMS FOR PERSONAL SPACES

(71) Applicant: Ecosense Lighting Inc., Los Angeles, CA (US)

(72) Inventors: Mark Reynoso, Los Angeles, CA (US); Benjamin Harrison, Los Angeles, CA (US); Paul Kenneth Pickard, Los Angeles, CA (US); Robert Fletcher, Los Angeles, CA (US)

(73) Assignee: KORRUS, INC., Los Angeles, CA (US)

( * ) Notice: Subject to any disclaimer, the term of this patent is extended or adjusted under 35 U.S.C. 154(b) by 0 days.

(21) Appl. No.: 17/185,579

(22) Filed: Feb. 25, 2021

(65) Prior Publication Data

US 2022/0047760 A1 Feb. 17, 2022

Related U.S. Application Data

(60) Provisional application No. 63/131,117, filed on Dec. 28, 2020, provisional application No. 63/064,596, filed on Aug. 12, 2020.

(51) Int. Cl.
*A61L 9/20* (2006.01)
*B01D 53/00* (2006.01)

(52) U.S. Cl.
CPC .............. *A61L 9/20* (2013.01); *B01D 53/007* (2013.01); *A61L 2209/134* (2013.01); *B01D 2259/4566* (2013.01); *B01D 2259/804* (2013.01)

(58) Field of Classification Search
None
See application file for complete search history.

(56) References Cited

U.S. PATENT DOCUMENTS

| 2006/0032199 A1 | 2/2006 | Beam |
| 2007/0207066 A1 | 9/2007 | Thur |
| (Continued) | | |

OTHER PUBLICATIONS

International Search Report dated Nov. 26, 2021 in International Application No. PCT/US2021/045708, 2 pages.
(Continued)

*Primary Examiner* — Jelitza M Perez
(74) *Attorney, Agent, or Firm* — FisherBroyles LLP

(57) ABSTRACT

An air purification system, includes a UVC light source arranged within an internal space of a purification chamber and adapted to irradiate the internal space with UVC, an airflow system arranged to introduce environmental air from outside of the air purification system into the internal space of the purification chamber and expel purified air from the purification chamber back outside of the air purification system, and a light blocking system arranged to block a substantial amount of the irradiated UVC from emitting outside of the air purification system, the light blocking system comprising a high-air-flow open structure mounted in the airflow system of the purification chamber, wherein the open structure comprises a front surface, rear surface and a thickness, wherein the front and rear surfaces have a plurality of open areas connected through the thickness, and wherein at least one of the plurality of open areas is of a size with respect to the thickness to block light from traversing the thickness when an angle of incidence is less than approximately 10 degrees.

6 Claims, 4 Drawing Sheets

(56) References Cited

U.S. PATENT DOCUMENTS

| | | | |
|---|---|---|---|
| 2010/0143205 A1* | 6/2010 | Engelhard | A61L 9/205 422/121 |
| 2015/0332425 A1* | 11/2015 | Kalanick | G07B 13/045 705/13 |
| 2017/0007736 A1 | 1/2017 | Engelhard | |
| 2017/0294130 A1 | 10/2017 | Donnelly | |
| 2019/0240370 A1* | 8/2019 | Benedek | A61L 9/122 |
| 2020/0079385 A1* | 3/2020 | Beaurepaire | B60W 60/0013 |
| 2020/0202148 A1 | 6/2020 | Wright | |

OTHER PUBLICATIONS

Written Opinion of the International Searching Authority dated Nov. 26, 2021 in International Application No. PCT/US2021/045708, 8 pages.

* cited by examiner

ANTIMICROBIAL SYSTEMS FOR PERSONAL SPACES

CROSS REFERENCE TO RELATED APPLICATIONS

This application claims the benefit of U.S. Provisional Patent Appl. No. 63/131,117, filed Dec. 28, 2020 and U.S. Provisional Patent Appl. No. 63/064,596, filed Aug. 12, 2020 the entire disclosures of which are incorporated herein by reference.

TECHNICAL FIELD

The present disclosure relates generally to systems and methods for purifying air utilizing UV exposure.

BACKGROUND

There is a need for improved cleaning systems designed to keep spaces and air clean, especially personal spaces. People are constantly in environments where there is little air exchange. People drive in cars, sleep in campers, work indoors, etc. People are also in common areas with other people where there is stagnant air or relatively low air exchange, such as in an airplane, bus, train, etc. People in these environments worry, or should worry, about microorganisms, bacteria, viruses and other harmful elements in the air. The inventors have discovered new and useful ways of combating the poor air conditions in such environments.

SUMMARY

In accordance with exemplary and non-limiting embodiments, an air purification system comprises a UVC light source arranged within an internal space of a purification chamber and adapted to irradiate the internal space with UVC, an airflow system arranged to introduce environmental air from outside of the air purification system into the internal space of the purification chamber and expel purified air from the purification chamber back outside of the air purification system, and a light blocking system arranged to block a substantial amount of the irradiated UVC from emitting outside of the air purification system, the light blocking system comprising a high-air-flow open structure mounted in the airflow system of the purification chamber, wherein the open structure comprises a front surface, rear surface and a thickness, wherein the front and rear surfaces have a plurality of open areas connected through the thickness, and wherein at least one of the plurality of open areas is of a size with respect to the thickness to block light from traversing the thickness when an angle of incidence is less than approximately 10 degrees.

In accordance with exemplary and non-limiting embodiments, a method comprises remotely instructing an air purification system situated in a car to operate to achieve a requested air quality the air purification system comprising a UVC light source arranged within an internal space of a purification chamber and adapted to irradiate the internal space with UVC, an airflow system arranged to introduce environmental air from outside of the air purification system into the internal space of the purification chamber and expel purified air from the purification chamber back outside of the air purification system and a light blocking system arranged to block a substantial amount of the irradiated UVC from emitting outside of the air purification system, the light blocking system comprising a high-air-flow open structure mounted in the airflow system of the purification chamber, wherein the open structure comprises a front surface, rear surface and a thickness, wherein the front and rear surfaces have a plurality of open areas connected through the thickness, and wherein at least one of the plurality of open areas is of a size with respect to the thickness to block light from traversing the thickness when an angle of incidence is less than approximately 10 degrees, and issuing instructions for the car to proceed to a pick-up location for a passenger.

DETAILED DESCRIPTION

Figure 1:
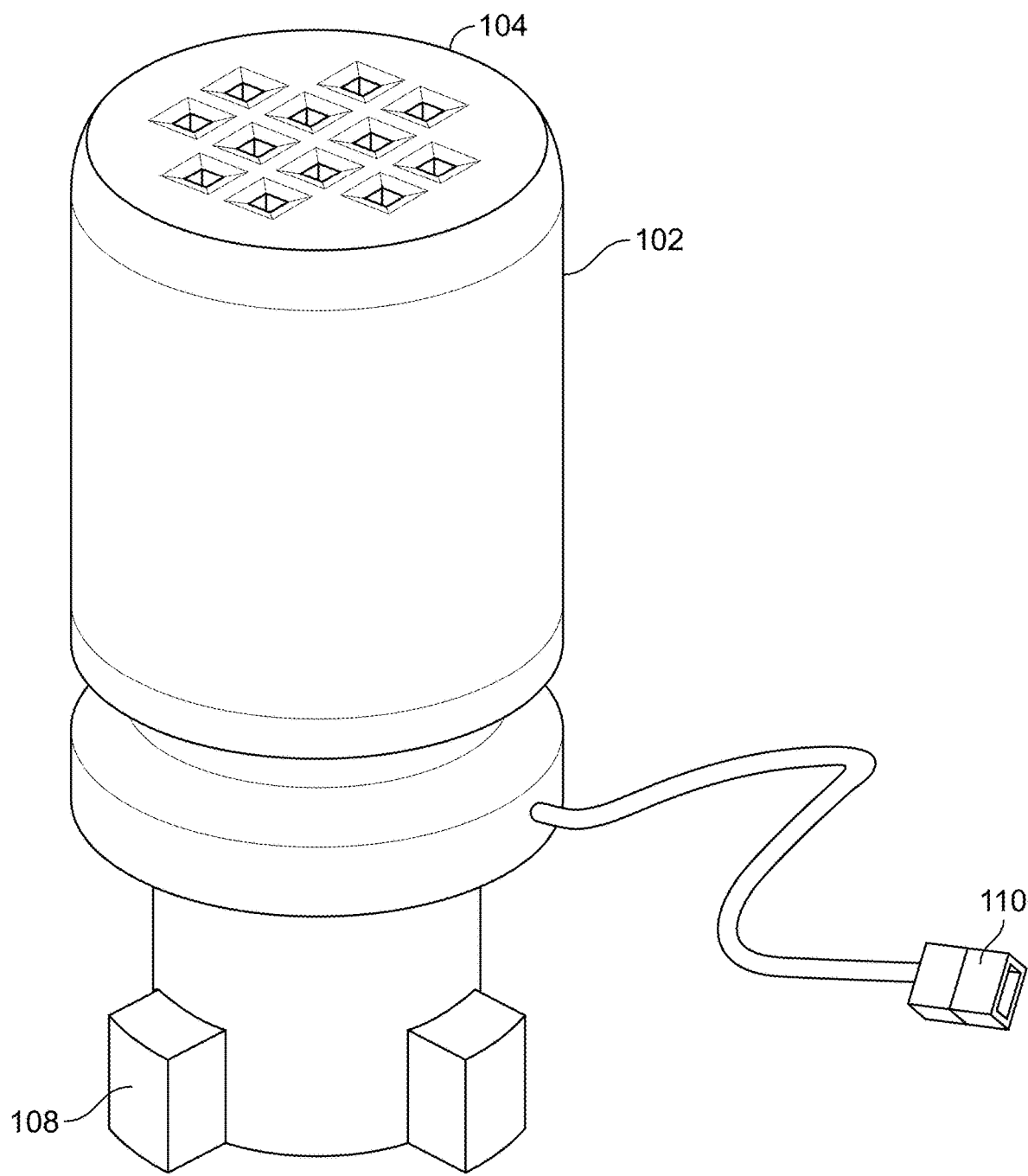
FIG. 1 illustrates an air purification system in accordance with the principles of the present invention.

As used throughout this application, the word "may" is used in a permissive sense (i.e., meaning having the potential to), rather than the mandatory sense (i.e., meaning must). The words "include," "including," and "includes" and the like mean including, but not limited to. As used herein, the singular form of "a," "an," and "the" include plural references unless the context clearly dictates otherwise. As employed herein, the term "number" shall mean one or an integer greater than one (i.e., a plurality).

As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other. Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

These drawings may not be drawn to scale and may not precisely reflect structure or performance characteristics of any given exemplary implementation, and should not be interpreted as defining or limiting the range of values or properties encompassed by exemplary implementations.

Unless specifically stated otherwise, as apparent from the discussion, it is appreciated that throughout this specification discussions utilizing terms such as "processing," "computing," "calculating," "determining," or the like refer to actions or processes of a specific apparatus, such as a special purpose computer or a similar special purpose electronic processing/computing device.

This disclosure includes a non-limiting set of embodiments used to describe certain inventions.

As used herein, "purified air" refers to air that results from the removal or deactivation of an amount of unwanted particulate matter in an initial quantity of air.

Indoor environments, enclosed environments, and places where people are in congested areas can be exposed to microorganisms, bacteria, viruses (e.g. CV-19) and other elements that can be harmful to the people's health. Described herein are new and useful technologies to help clean the air in such environments. The inventors have also discovered new and useful personal space airflow cleaning systems.

FIG. 1 illustrates an exemplary and non-limiting embodiment of a personal space air cleaning device 102. This embodiment shows a cup holder mount 108 mechanically arranged to fit into a car or other vehicle's cup holder. This is one example of a mounting system; others are encompassed by this disclosure. This embodiment also illustrates a USB connector 110, which may supply power and/or data to the cleaning device 102. This is one example of a power and/or data system; others are encompassed by this disclosure. There is also a vent 104 at the top of the cleaning device 102. The vent 104 may be placed in any useful position on the cleaning device 102. The vent facilitates air flow through the cleaning device 102 by provide an escape for the air passing through the cleaning device 102.

Internally (not shown in FIG. 1 but illustrated in FIG. 2), the system may include an ultraviolet lighting system 210 (e.g. LED, low pressure discharge, high pressure discharge, fluorescent), fan, internal airways to direct the flow of the air, filter (e.g. HEPA, micron level, dust level), electrical, liquid, vapor or solid air cleaning systems (e.g. charcoal, disinfection solution).

The cleaning device 102 may be arranged to pull air into the device (e.g. electric fan, passive airflow system (e.g. using heat differential in the device 102)). The airflow may be directed to pass the ultraviolet lighting system where the ultraviolet light disinfects and/or harms and/or kills microorganisms, bacteria, viruses and/or other elements in the airstream. The airstream may then flow out of the vent 104. In embodiments, the air passes through a filter before being directed through the vent 104, either before or after passing through the UV light. In embodiments, the air may be exposed to other air purification materials, such as charcoal or disinfecting liquid or spray.

Figure 2:
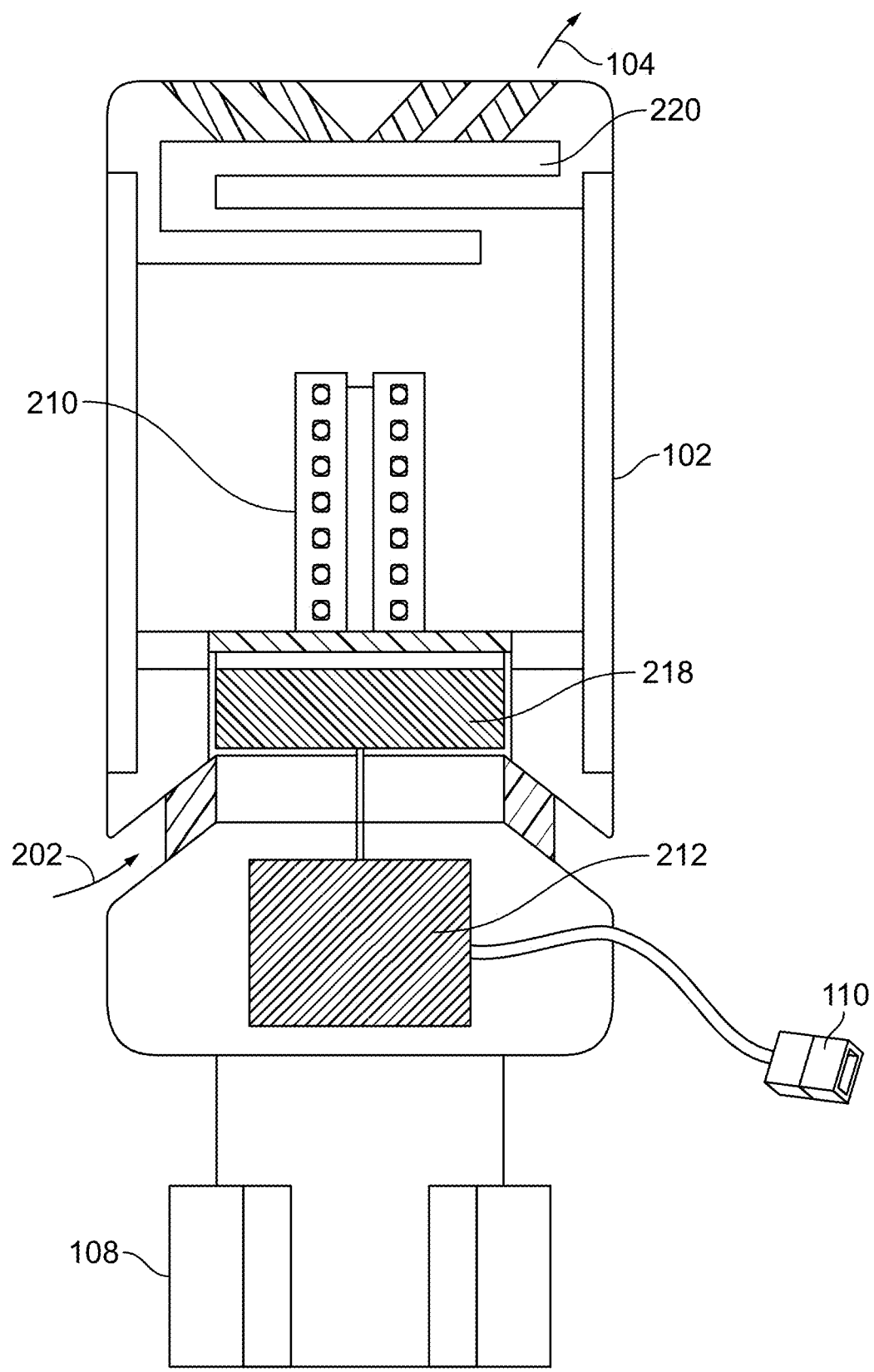
FIG. 2 illustrates an internal cut-away perspective view of an air purification system in accordance with the principles of the present invention.

FIG. 2 illustrates an exemplary and non-limiting embodiment of a cut-away perspective of the cleaning device 102. As can be seen in the figure, the cleaning device 102 includes an ultraviolet lighting system 210 to produce UVA, UVB, UVC, near UV (e.g. violet), etc. As air flows past the ultraviolet lighting system 210 the air can be cleaned by removing, harming or killing microorganisms, bacteria, viruses and other airborne harmful agents. The cleaning device may also have a fan 218, intake vents 202, and air direction systems 220 (e.g. baffles) to force the environment's air to pass by the ultraviolet lighting system and back into the environment. The cleaning device 102 may also include a power and/or data system 212 to facilitate powering of the fan 218 and the ultraviolet lighting system 210. The power and/or data system 212 may be electrically connected to the connector 110 (e.g. USB connector) that is intended to be plugged into a power source (e.g. the vehicle's system, external battery).

In embodiments, the air direction system may serve as a light blocking element in addition to or in place of the air handling function. The ultraviolet light produced by the ultraviolet lighting system 210 may be better contained within the cleaning device with such an arrangement while allowing proper air flow.

In embodiments, the cleaning device 102 may process air at a rate that is roughly equal to outside air entering the personal environment. In other embodiments, the processing rate is based on the level of exposure to poor air quality that is expected in the environment. If the vehicle is used as a ride sharing vehicle where unknown people are entering the car throughout the day the rate may be set based on an expected air contamination rate by infected people. In embodiments, the rate may be based on the volume of space in the environment that you are trying to clean. For example, the system may be designed to exchange a car's cabin air at a rate of 0.5 air changes per hour. A subcompact car may be around 85 cubic feet, so the system may produce 0.7 cfm of clean air. This could be done with a 1 cfm flow and 30 mW of UV. This is merely an example flow and UV power that may be useful. In embodiments, the flow rate and UV power may be adapted for a given application (e.g. cabin size or volume of personal space on a plane). As another example, the system may be designed for approximately 15 cfm with 1.5 watts of UV.

In embodiments, the mounting system may be a cup holder mount, clip-on mount, screw-in mount, magnetic mount, dashboard mount, internal roof mount, seat mount, headrest mount, floor mount, door mount, another systems ventilation system (e.g. mount on a car's vent so the air forced through the car's vent goes through the cleaning device, mount on an airplane's personal vent positioned to pass air to person in the seat), personal attachment system (e.g. lanyard, neck pillow, neck speaker, neck bone conduction system, within or on a hat or helmet), etc.

In embodiments, the cleaning device 102 may be mounted on a vent of another system (e.g. car's vent, airplane's vent). The air flow provided by the car or other ventilation system may force air through the cleaning device and into the associated environment. An internal cleaning device fan or other airflow system may not be included in such an embodiment. The UV lighting system 210 may be battery powered, USB powered, wirelessly powered, internal impeller powered where the vehicle's vent system's airflow, etc.

In embodiments, the cleaning device may be mechanically adapted to fit inside the vehicle's ventilation system (e.g., at or near the exit of the airflow system, inlet of the airflow system, or otherwise positioned). For example, as an aftermarket product, a user may remove the vent cover on a car's ventilation system, then fit the cleaning device into the vent for secure mounting. The vent cover may be replaced to maintain the OEM look of the dashboard or the cleaning device may have an attractive exit vent that replaces the car's original one.

Aspects of the present embodiments relate to purifying air in a monitored environment. Monitoring the environment may be more effective and pleasant to the occupants than purifying the environment without such consideration.

There are a number of ways to purify air (e.g. pushing the air through a Hepa filter, irradiating the air with ultraviolet light (e.g. UVA, UVB, UVC, deep UV (e.g. approx. 222 nm), and/or irradiating the air with violet light, etc.). The entire environment may be irradiated with UV but this generally requires that no one is in the environment because UV can be harmful to humans. The environmental air may also be pushed past a chamber that is irradiated with UV such that the air is purified, and the ultraviolet light is contained.

In embodiments, ultraviolet light irradiates the inside of a reflective chamber and an airflow system is arranged to push or pull the environmental air into the chamber for purification and back out into the environment. The ultraviolet light source (e.g. LED, discharge tube, low pressure discharge tube, high pressure discharge tube, etc.) may be geometrically arranged to project the ultraviolet into the reflective chamber such that the rays of ultraviolet light reflect off of the surfaces of the chamber multiple times. The reflected light design can increase the purification efficiency because the light interacts with more air. The chamber may include multiple surfaces (e.g. the inside of a box configuration) or one surface or portion of a surface. The chamber may have an inlet and outlet to guide the air through the purification system and the inlet and outlet may be made of reflective material. The reflective material may be aluminum, which is approximately 70% reflective in the UVC band. Polished aluminum is slightly more reflective. The reflective material may be steel or stainless steel, or polished stainless steel, which is approximately 40% reflective in the UVC. The reflective material may be Polytetrafluoroethylene (PTFE), which is a synthetic fluoropolymer of tetrafluoroethylene. PTFE is highly reflective in the UV range; in the UVC range it can be between 80 and over 95% reflective. The reflectivity of the PTFE may depend on the thickness of the material. For example, a PTFE thickness of 0.19 mm may exhibit an average reflectivity between 250-400 nm of approximately 80% and an average reflectivity between 400-800 nm of approximately 76% while a PTFE thickness of 2 mm may exhibit an average reflectivity between 250-400 nm of approximately 97% and an average reflectivity between 400-800 nm of approximately 97%.

In general, the reflectivity of a material is strongly positively correlated to the number of a times a photon may be reflected.

For example, a material with 30% reflectivity may produce a few reflections of a light ray while a material with 98% reflectivity may produce 50 or more reflections of the light ray. The increased number of reflections, as noted above, may increase the efficiency of the purification process. Cost and other consideration may cause a product designed to make a choice other than the most reflective material, however, the most efficient purification system has a geometric configuration to encourage reflections within the chamber and a material with the highest reflectivity in the particular range of the ultraviolet spectrum that is being used to purify the air (e.g. UVC).

Other materials may be used as the reflective material in the chamber; the examples provided herein are not the only materials one may choose to use. Further, the material may be bulk material, sprayed on material, deposited material, heat treated material, etc.

The purification system may have a computer system, or other electronic system, to monitor and/or control the performance of the purification system. UV lamps may be sensitive to temperature. Operating a low-pressure mercury lamp, for example, in a very cold environment may decrease the lamp's output. The computer system may receive sensor feedback relating to the temperature of the lamp(s), chamber environment or other area in or around the purification system. The computer system may cause the temperature in the purification system (e.g. in the chamber) to be regulated based on the temperature feedback. The computer system may regulate the power delivered to the light source to increase or decrease its output. UV lamps may also decease in output over their life span. The computer system may receive sensor feedback relating to the amount of UV being produced, the age of the lamp(s) or other information and regulate the purification system accordingly. For example, if there is an indication (e.g. based on the age of the lamp(s) or sensor feedback of the temperature or output) that the output of the lamp(s) has dropped, the computer system may increase the power to the lamp(s), change the temperature of the area near the lamp(s), change the power delivered to a fan in the airflow system, etc. Decreasing the airflow through the chamber can increase the time the air is exposed to the UV radiation, which can compensate or partially compensate for reduced output from the lamp(s). The computer system may monitor the lamp and fan by monitoring their voltage, current, power, output, temperature, etc.

The computer system may be associated with environmental sensors and/or data feeds that provide information about the environment such that the purification system can regulate its performance. The environment may be monitored for carbon dioxide, temperature, moisture, etc. as an indication of the number of people in the area. The computer system may receive data indicating the number of occupants (e.g. from a phone app, seat sensors in a vehicle) The computer system may regulate the performance of the purification system based on thresholds, patterns, machine learning, etc. from the sensors. For example, the purification system may be mounted in the cabin of a vehicle (e.g. car, truck, bus, Uber, taxi) or in the air handling system of the vehicle and the purification system may regulate its performance based on how many occupants are in the vehicle.

The vehicle may be used for sharing a ride or as a car for hire so the number of occupants may change frequently and have unknown people in the car with an unknown medical history or conditions. If one person is in the vehicle the purification system may regulate itself to a low, maintenance mode (e.g. medium power setting on a fan circulating the air or medium power on the lamp), to maintain the air that is already been purified and is only potentially being contaminated by the one person. If the one person's health is verified as acceptable, the purification system may turn itself off or to a very low mode (e.g. very low fan setting or lamp power setting). If more than one person is in the vehicle the purification system may turn up the performance (e.g. higher fan setting or lamp power setting). While the sensor feedback may be indicative of the number of occupants, the sensor feedback may be used to understand the condition of the environmental air. If the carbon monoxide is high, for example, the purification system may increase its purification rate regardless of the number of occupants. The purification system may be programmed to target a specific pathogen or set of pathogens and it may regulate itself in part based on the known science about such pathogen.

The computer system may communicate data to other systems. The purification system may communicate air quality or purification performance information to another system for monitoring and/or verification. For example, in a vehicle used for ride sharing or car for hire the purification system may be connected to a ride share phone app (e.g. Uber, Lyft) and the ride share app may monitor and verify that the purification system is operating to specification and that the air quality is acceptable. The driver and the rider(s) may be notified of the compliance, the performance, or the air quality.

As another example of purification based on an environmental awareness, the purification system may receive data from another system (e.g. a ride sharing app) indicating the vehicle is about to pick up a rider(s) and the purification system, as a result, may increase its purification performance before the riders are picked up. Similarly, the ride sharing app may indicate that riders have just been dropped off at their destination and the purification system may increase its performance for a period of time to prepare the cabin for new riders. The new riders may be provided an indication that the cabin has been purified.

Figure 3:
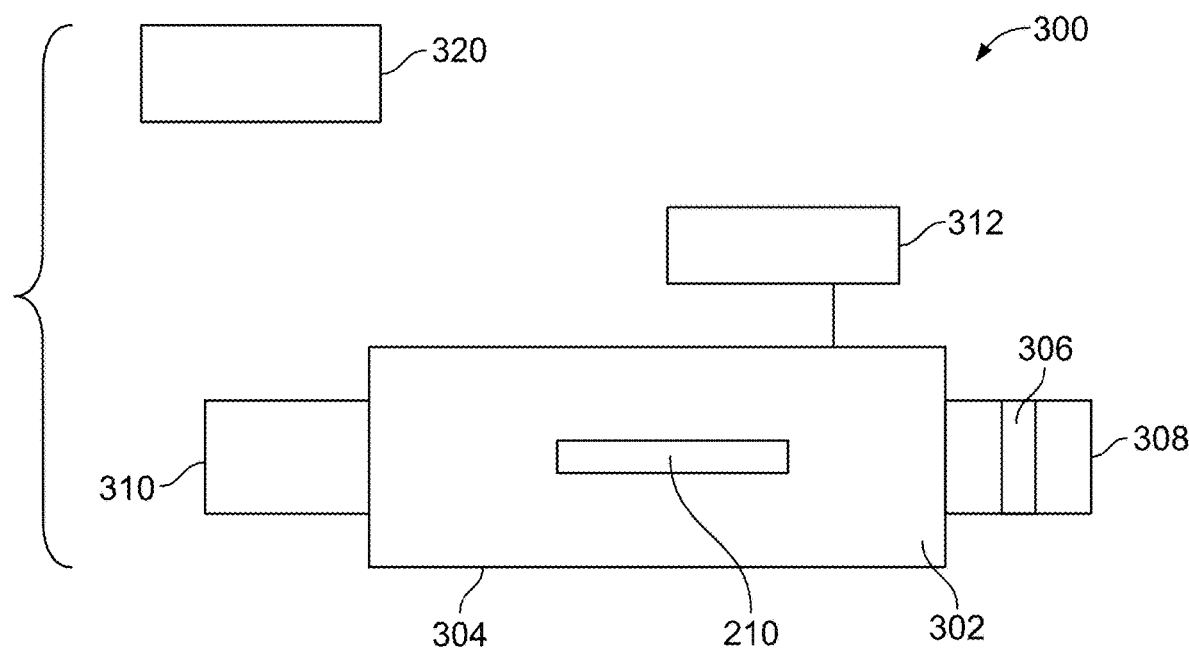
FIG. 3 illustrates a block diagram of a purification system in accordance with the principles of the present invention.

FIG. 3 illustrates a block diagram of an air purifying system according to the principles of the present inventions. The system includes a low resistance airflow system causing environmental air to pass through a chamber irradiated with UVC, wherein the chamber 302 has at least one surface 304 with a UVC reflectivity at or above approximately 50%. As described herein, the reflectivity is generally a function of the type of material and the surface condition of the material, including any materials treating the surface. Reflectivity may exceed 90 to 95% by using a PTFE material. The geometric configuration of the chamber 302 and the UVC lamp affects the number of reflections of light rays within the chamber. The chamber may include multiple surfaces 304 (e.g. substantially all of the chamber's internal surfaces) of high reflectivity with the lamp 210 positioned to irradiate in a direction to encourage many reflections to increase the purification efficiency of the system.

The purification system may also include an airflow system with an inlet to introduce the environmental air to the chamber and an outlet to reintroduce treated air back into the environment. The system may be geometrically arranged such that all UV radiation is contained within the purification system or within the chamber itself. The containment arrangement may include materials that absorb or reflect the UVC (e.g. as disclosed herein elsewhere).

The purification system may have an electronic control system 312 (e.g., computer system, passive circuitry, active circuitry, single processor, multiple processors, on-board systems, remote systems and combinations thereof). The control system may control the speed of a fan 306 pulling the environmental air into the inlet. The fan may be configured in a number of places in or on the purification system (e.g., in the inlet, outlet or chamber). The fan may have multiple speed settings (e.g., discrete, substantially continuous or continuous) that may be controlled by the control system 312.

In embodiments, the control system may regulate the speed settings and/or lamp settings depending on an environmental condition. The environmental condition may be assessed through sensors gathered information and/or data from other computer systems 320. For example, if the environmental condition is determined as clean, the speed and/or lamp settings may turn down or even turn off. If the condition is clean and human occupancy indicated, the settings may be increased to maintain the clean air. If the occupancy is high then the setting may be set to a high setting.

The purification system may be aware of, programmed for or pre-programmed for the size of the environment such that it can control itself based on the air quality and occupancy in a way as to purify the air within a certain amount of time. For example, if the environment is the inside cabin of a four-door sedan, with a known range of typical cabin volumes, the purification system may control itself to clean the entire volume within a period of time (e.g. 30 seconds, 60 seconds, minutes, etc.). If the occupancy of the known environment volume is known and/or the air quality is known than the purification system may regulate itself to clean the volume of air within the specified time.

Embodiments of the present inventions may or may not include air filter(s). Generally speaking, Hepa filters are used to physically capture very small particles from air passing through them. A significant draw back from Hepa or other small pore filters is that they restrict airflow such that more head pressure is needed to push the air through the filter. This tends to necessitate a high electric powered air handling system if a high air exchange volume is intended. In embodiments, a filter with relatively high porosity may be included in the airflow system to capture larger particles (e.g. dust and dirt) while maintaining a low head pressure for a low resistance airflow system. In embodiments, the purification system may not include a filter (e.g. when the main objective is to purify the air with the highest throughput capacity at a energy consumption target). In embodiments, the porosity of a filter included in the purification system may capture particles larger than about 10 microns, 5 microns, 3 microns, and 1 micron.

The fan 306 may be a single fan or multiple fans. Multiple small fans may produce less noise and so may be preferable for quieter environments or where the noise is just not wanted. Multiple fans also make for the availability of different form factors for different environment constraints.

The air purification system's electronic control system may control various aspects of the purification system based on sensor feedback (e.g., from a carbon dioxide sensor, proximity sensor, occupancy sensor, seat sensor, etc.) or based on information provided by another system 320 (e.g., data indicating a past, current or future venue occupancy, date from a reservation system, data from a ride sharing app).

In embodiments, the sensor(s) may measure carbon dioxide in the environment, changes of the composition in the air in the environment, thermal change in the air, image analysis, wireless transmission detection (e.g., Bluetooth, Wifi) in the environment, sitting position sensors, motion sensor, weight sensor, etc.)

Sensor fusion and data analysis of several sensors and/or other data and information sources may be used by the purification system to regulate itself such that purification goals are achieved. For example, if the carbon dioxide increases and the temperature in the environment increases, a correlation may indicate that one or more people have been added to the environment. If an additional Bluetooth, Wifi, cell communication, or other wireless transmission is detected, it may indicate that someone has come into the environment. The strength of the signal(s) may indicate if the new person(s) is in the environment to be purified or further removed from the environment. If a car is parked, a motion sensor and/or weight sensor may indicate someone has entered or exited the car. Door and seat sensors in a car may be used as well. Image sensors in the environment may produce data that shows how many people are in the environment and what position they are in within the environment. The purification may use the image data/analysis to regulate the efficiency and change the direction of the airflow in the purification system. In embodiments, any combination of two or more sensors may be used to predict an environmental condition that may affect the air quality in the environment to the purified.

The purification system may receive data from other computer systems to create environmental awareness and the purification system may adjust its performance in an effort to purify the air within a predetermined period of time. For example, the purification system may receive data relating to the environment that is to be purified from a mobile phone app, local computer system, networked computer system, etc. The data feed to the purification system may be from a reservation system, air quality system, weather system, ride share service, etc.

For example, the computer information from another source may be for the detection of occupancy as determined by a reservation system. A reservation system may take reservations from a person intending to arrive at a certain time with a number of people and the reservation system may predict or be set to estimate when the people will be leaving. This, and other, information may be sent to the purification system and the purification system can regulate itself to purify the relevant environment before the estimated arrival time and then, at least initially, regulate itself to maintain a purification level based on the number of people expected based on the reservation. Sensor and other feedback may inform how the purification system should regulate itself through the reservation period. The reservation system may service a restaurant, car for hire, ride sharing vehicle, airplane, bus, train, etc.

A ride sharing app may have a reservation feature that identifies one or more people that are going to be picked up at a certain time and then the ride will likely last a predicted period of time. The reservation function may also indicate when the one or more people have left the vehicle, which may be at different times. Such information may be communicated to the purification system and the purification system may use it to regulate itself before, during and after the ride.

In some embodiments, a ride sharing app may operate to enforce a uniform air quality standard. For example, a ride sharing company or entity providing automobile rides via a ride sharing app may receive requests from a user of the app for the provision of a ride. In such instances, when selecting a car and attendant driver to be assigned the task of picking up the user and delivering the user to a requested destination, the system may consider a variety of attributes such as distance from the driver to the user, make and model of the car and the like. In addition, the system may receive data indicative of an air quality in the vehicle. The system may use this indication of air quality when determining how best to meet the needs of the user.

In some embodiments, the system may not consider for ride fulfillment purposes any car that is currently exhibiting an air quality below a required level. Such a level may comprise a predetermined constant among all cars in a fleet. In other embodiments, the required air quality may be user defined via, for example, a ride share app and may be associated with a user's ride sharing app profile.

In other embodiments, the system may consider the provision of cars to users in instances where a car has a present air quality below the required level. For example, the system may determine that, but for an at present below required air quality level, a specific car would be preferable to assign to a ride sharing request from a user. The system may determine that it will take, for example, seven minutes for the car to get to an agreed upon pick-up spot for the user. The system may further determine that the in-car cleaning device, if activated, is capable of achieving the required air quality level in the seven minute time period. The system may then operate to assign the car to fulfill the user's ride request while transmitting an instruction to the car's cleaning device to commence operation so as to achieve the required air quality prior to arriving at the user's location.

In some embodiments, a user's ride sharing app may provide for real-time or near real-time updates of the air quality in a vehicle selected by the system to provide a ride sharing service. For example, in addition to providing a user with, for example, an identity of a driver and the make and model of the car assigned to provide a ride to the user, the user may be further enabled to view, such as on the ride sharing app operating on a smart phone, the air quality of the car.

The purification system may have data indicative of the size of the reserved space or it may be sized for a size or range of sizes. The purification system may use the size of the environment in its calculations of how to regulate itself to attain the air purification goals of the environment. For example, a ride share vehicle of a known cabin size may have a purification system installed. The purification system may go into a high clean air delivery rate "CADR" to prepare the cabin for occupancy of the passengers. An example of a high CADR may be a rate that exchanges 50% or more of the cabin volume per minute. This may have a rate of 40 cubic feet per minute "CFM". A medium CADR may be between 25% and 50% of the cabin volume per minute. A low CADR rate may be less than 25% of the cabin volume per minute.

The purification system may provide feedback to the reservation system to indicate conditions of the air in the environment and the condition of the purification system itself. The feedback may provide an indication that the environment is ready for occupancy, not ready for occupancy, purification system is working to specification, purification system is not working properly, etc. Information based on the purification system feedback may be communicated to the driver of a ride share vehicle, passenger or to-be passenger of the ride share, and/or the corporation facilitating the ride share to inform about the condition of the environment and/or purification system. This information may provide a reassurance that the environment and systems are in compliance. The corporation facilitating the ride share may program the app or supporting system to cause a vehicle to go 'off-line' and not accept passenger if it is not in compliance.

A purification system according to the principles of the present inventions may be networked or otherwise coordinated with one or more other purification systems in a larger environment. For example, a large indoor space (e.g., restaurant, office, retail shop, etc.) may have more than one purification system placed in different areas within the large indoor space and they may be coordinated to purify their respective areas based on sensor and or data feeds. Such purification systems may be inside the facilities HVAC air handling system, separate from the HVAC system, stand-alone units, etc.

A purification system according to the principles of the present inventions may be arranged as a personal space purifier used in a larger environment. For example, the purification system as described herein may be small enough to mount on or around a tabletop (e.g. at a restaurant). It may have environmental awareness, through sensor feedback and/or data received otherwise, and be of a capacity to purify air and maintain pure air in an environment in and immediately around the table.

Figure 4:
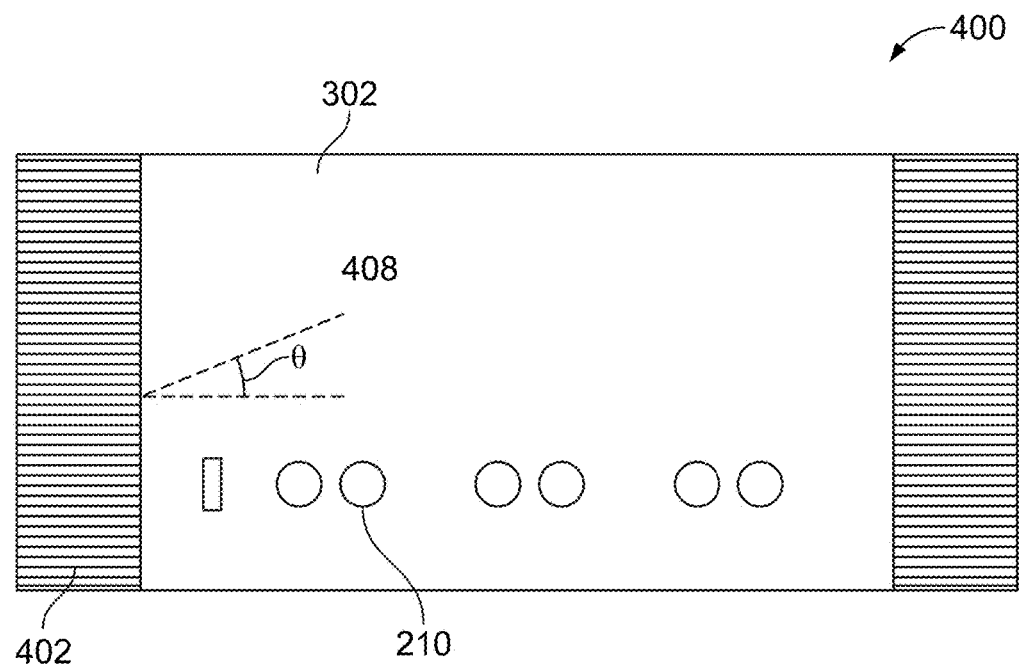
FIG. 4 illustrates a cross sectioned block diagram of a purification system in accordance with the principles of the present invention.

FIG. 4 illustrates an exemplary and non-limiting embodiment of a high-flow purification system cross sectional view 400. The purification system 400 has a chamber 302 with one or more UVC light sources 210, as described herein. The system includes a highly porous end cap 402 on each end of the chamber. The highly porous end caps 402 have large pores such that air can flow easily through them. The pores have a width (further explained below) to create a low angle of acceptance 408 (e.g. 10, 9, 8, 7, 6, 5, 4, 3, 2, 1 and less than 1 degree) for any light to escape the chamber. This causes substantially all light arriving at the end cap 402 that is outside of the low angle acceptance 408 to be reflected or absorbed. A light blocker (e.g. UVC opaque material, UVC reflective material, UVC absorbent material, coated material, metal oxide coated material, plastic, stainless steel) 404 is geometrically arranged with respect to the light sources 210 such that it blocks light from any of the UVC light sources from encountering an end cap at an angle less than the low acceptance angle 408. This configuration can prevent UV light from escaping the chamber while producing a high-flow, low air resistant, purification system. This is only one example of the many that are envisioned. In some embodiments, the endcaps are made of a material that is generally light absorbing, particularly UV light.

Figure 5A:
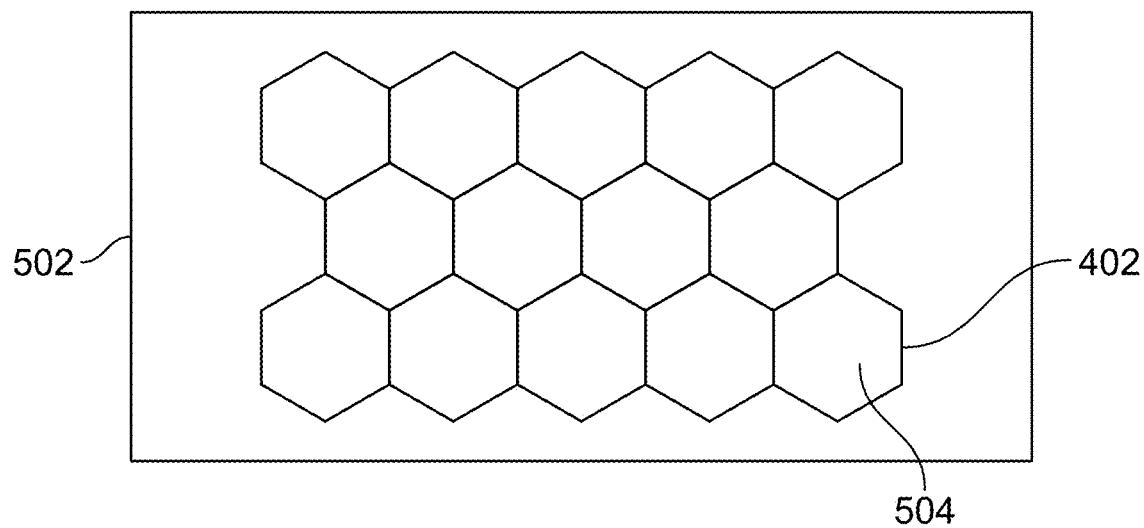
FIGS. 5A and 5B illustrate an end cap design in accordance with the principles of the present invention.

FIG. 5A illustrates an exemplary and non-limiting embodiment of an end view of a portion of the end cap 402. It is designed with a honeycomb open structure. While this configuration depicts hexagon shaped pores 504, it should be understood that other shapes (e.g. round, square, other polygons) would operate well. The pores 504 depicted in FIG. 5A are approximately ⅛" across. This is an example size, and the size could be much smaller (e.g. down to the size of a dust filter) or larger and the light blocker could be sized and positioned to block the light from hitting the end cap 402 within the low angle of acceptance 408.

Figure 5B:
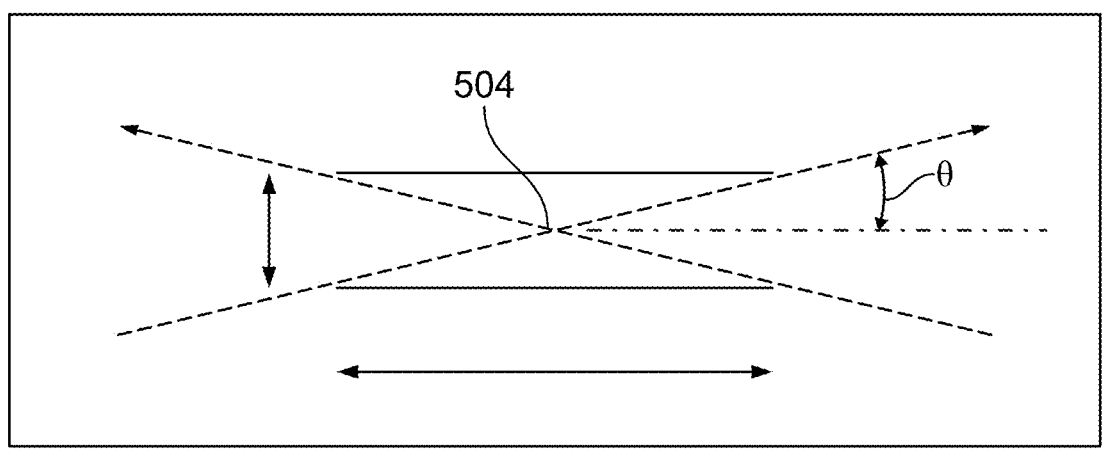

FIG. 5B is an exemplary and non-limiting embodiment of a side cross section view of one pore 504. As is noted, the pore may be approximately ⅛" across and approximately 1" long. The angle of acceptance 408 is small as illustrated by the transmission of the photons.

The invention claimed is:

1. An air purification system, comprising:
   a UVC light source arranged within an internal space of a purification chamber and adapted to irradiate the internal space with UVC;
   an airflow system arranged to introduce environmental air from outside of the air purification system into the internal space of the purification chamber and expel purified air from the purification chamber back outside of the air purification system; and
   a light blocking system arranged to block a substantial amount of the irradiated UVC from emitting outside of the air purification system, the light blocking system comprising a high-air-flow open structure mounted in the airflow system of the purification chamber;
   wherein the open structure comprises a front surface, rear surface and a thickness, wherein the front and rear surfaces have a plurality of open areas connected through the thickness, wherein the air purification system is situated within a car and is in communication with a ride-share service used to arrange pick-up and drop off of a passenger, and wherein the air purification system is adapted to receive from the ride-share service an instruction to activate operation of the air purification system to achieve a predetermined air quality, and wherein the air purification system is further adapted to transmit to the ride-share service an indication that the predetermined air quality has been achieved.

2. The air purification system of claim 1, wherein the plurality of open areas are arranged in a shape selected from the group consisting of a honeycomb shape, a circular shape, a square shape, a rectangular shape, a linear shape, and a circular shape.

3. The air purification system of claim 1, wherein at least one of the plurality of open areas is approximately ⅛" in a major diameter and the thickness is approximately 1".

4. The air purification system of claim 1, wherein the predetermined air quality is determined by the ride-share service.

5. The air purification system of claim 1, wherein the predetermined air quality is determined by the passenger.

6. An air purification system, comprising:
   a UVC light source arranged within an internal space of a purification chamber and adapted to irradiate the internal space with UVC;
   an airflow system arranged to introduce environmental air from outside of the air purification system into the internal space of the purification chamber and expel purified air from the purification chamber back outside of the air purification system; and
   a light blocking system arranged to block a substantial amount of the irradiated UVC from emitting outside of the air purification system, the light blocking system comprising a high-air-flow open structure mounted in the airflow system of the purification chamber;
   wherein the open structure comprises a front surface, rear surface and a thickness, wherein the front and rear surfaces have a plurality of open areas connected through the thickness, wherein the air purification system is situated within a car and is in communication with a ride-share service used to arrange pick-up and drop off of a passenger, and wherein the air purification system is adapted to receive from the ride-share service an instruction to activate operation of the air purification system to achieve a predetermined air quality, and wherein the ride share service is adapted to transmit to the indication of the air quality to a prospective passenger of the ride-share service.

* * * * *